United States Patent [19]

Berka et al.

[11] Patent Number: 5,498,529
[45] Date of Patent: Mar. 12, 1996

[54] PROTEIN PROTEASE INHIBITORS FROM STREPTOMYCES

[75] Inventors: Thomas R. Berka, Wyncote; James A. Fornwald, Norristown; Joselina G. Gorniak, Willow Grove; Martin Rosenberg, Royersford; James E. Strickler, Havertown; Dean P. Taylor, King of Prussia, all of Pa.

[73] Assignee: SmithKline Beckman Corporation, Philadelphia, Pa.

[21] Appl. No.: 162,506

[22] Filed: Dec. 3, 1993

Related U.S. Application Data

[63] Continuation of Ser. No. 894,167, Jun. 3, 1992, Pat. No. 5,279,939, which is a continuation of Ser. No. 346,119, Feb. 16, 1989, abandoned, which is a continuation-in-part of Ser. No. 897,245, Aug. 18, 1986, abandoned.

[51] Int. Cl.$^6$ .................................................. C12P 21/00
[52] U.S. Cl. ........................ 435/69.1; 435/69.2; 435/69.7; 435/69.8
[58] Field of Search ................................. 435/6, 7, 69.2, 435/252.3, 172.3, 320.1, 252.35, 29.34, 35, 91.1, 172.1, 172.2, 886, 887, 69.1, 69.7, 69.8; 530/350, 825; 536/23.7, 23.4; 935/11, 14, 41, 47, 61, 72, 75, 81

[56] References Cited

U.S. PATENT DOCUMENTS 5,279,939  1/1994  Berka et al. ............................... 435/6

FOREIGN PATENT DOCUMENTS 833987  2/1985  South Africa .

OTHER PUBLICATIONS

Helfman et al., Proc. Natl. Acad. Sci. USA 80: 31 (1983).
Verweij et al., Nucleic Acids Res. 13: 4699 (1985).
Young et al., Proc. Natl. Acad. Sci. USA 80: 1194 (1983).
Ikenaka et al., J. Biochem. 76: 1191 (1974).
Sugino et al., J. Biol. Chem. 253: 1546 (1978).
Bezborodov et al., Chem. Abstr. 102: 217993k (1985).

Primary Examiner—James Martinell
Attorney, Agent, or Firm—Herbert H. Jervis; Edward T. Lentz; Stuart R. Suter

[57] ABSTRACT

This invention relates to a process for producing a heterologous polypeptide in *Streptomyces* which involves transforming a *Streptomyces* organism with a recombinant DNA molecule comprising an LEP-10 of LT1 sequence selected from the group consisting of a sequence encoding a gene expression unit, a promoter sequence or an export control encoding sequence each operatively linked to a heterologous coding sequence and then culturing the transformed *Streptomyces* such that the heterologous polypeptide is expressed.

1 Claim, No Drawings

PROTEIN PROTEASE INHIBITORS FROM STREPTOMYCES

CROSS REFERENCE TO RELATED APPLICATIONS

This application is a continuation application of U.S. application Ser. No. 07/894,167, filed Jun. 3, 1992, now U.S. Pat. No. 5,279,939, which was a continuation of U.S. application Ser. No. 07/346,119, filed on Feb. 16, 1989, now abandoned, based on International Application PCT/US87/02009 file Aug. 17, 1987 and which designated the United States and which was a Continuation-in-Part of U.S. application Ser. No. 06/897,245, filed Aug. 18, 1986, now abandoned.

FIELD OF THE INVENTION

This invention relates to microbial protease inhibitors and, specifically, to protein pretease inhibitors produced by *Streptomyces*, which are structurally related to *Streptomyces* Subtilisin Inhibitor, and cloned genes and uses thereof in recombinant DNA processes.

BACKGROUND OF THE INVENTION

Protein protease inhibitors appear to-play a role in regulation of protease functions in living organisms and cells. Such protease inhibitors are widely distributed in animals and plants. Exemplary of these are alpha-1-antiprotease, soybean trypsin inhibitor, bovine pancreatic trypsin inhibitor and antithrombin. Microbially produced protein protease inhibitors include a family of dimeric proteins, each 10 to 12 kilodaltons (kd). This family includes SSI, alkaline protease inhibitor (API-2) from *S. griseoincarnatus*, plasminostreptin (PSN) from *S. antifibrinolyticus* and a protease inhibitor from *Streptoverticilium cinnamoneum*. The inhibitors of the SSI family share extensive sequence homology, e.g., about 70% between SSI and PSN, but appear to have different protease specificities. See, generally, "Protein Protease Inhibitors - The Case of *Streptomyces* Subtilisin Inhibitor (SSI)", edited by Hiromi et al., Elsevier, 1985, pages 1–14, 139–161 and 365–395. Kakinuma et al., U.S. Pat. No. 4,014,860, disclose PSN and a producing strain thereof.

Protein protease inhibitors have medical application such as in treatment of lung tissue degradation caused by deficiency in alpha-1-antiprotease. Protein protease inhibitors can also be utilized to prevent protein degradation caused by proteases such as are present in serum. Wilson, EP-A-113,319, report use of *Erythrina* trypsin inhibitor to inhibit conversion of one chain tissue plasminogen activator to the two chain form which occurs in a presence of serum.

*Streptomyces* are an attractive host for production of desired polypeptides by recombinant DNA techniques because they possess the necessary cellular "machinery" to export proteins and because a great deal of experience in culturing *Streptomyces* for antibiotic production has been acquired.

A problem which has been encountered in production of heterologous proteins in *Streptomyces* is protein degradation by endogenous proteases. A second problem which has been encountered is in obtaining export signal sequences which can be fused to heterologous coding sequences to direct export of heterologous gene products.

Furthermore, it is desirable to obtain regulatory regions, e.g., promoters, ribosome binding sites and transcriptional enhancing/stabilizing sequences which can be used to express heterologous coding sequences in *Streptomyces* at high levels. Such promoters are typically associated with production of abundant mRNA and/or gene products.

Brawner et al., EP-A-187,630 disclose a *Streptomyces* beta-galactosidace gene expression unit and use of the promoter and of the export signal sequence thereof to express and export heterologous gene products.

It is an object of the present invention to provide novel protein protease inhibitors from *Streptomyces*. It is a further object to provide small exported proteins, which are exported and which are produced in abundant amounts, and DNA coding sequences, export signals and regulatory regions therefor.

SUMMARY OF THE INVENTION

The invention is of novel protein protease inhibitors selected from the group consisting of Lividans Exported Protein (10 kd) (LEP-10) and Longisporus Trypsin Inhibitor (LTI).

In further aspects of this invention, the invention is a recombinant DNA molecule comprising (i) the LEP-10 or LTI gene expression unit, (ii) the LEP-10 or LTI coding sequence (iii) the LEP-10 or LTI regulatory region (iv) the LEP-10 or LTI export signal sequence or (v) a hybrid coding sequence having a portion of the LEP-10 or LTI coding sequence fused to a heterologous coding sequence and a microorganism or cell transformed therewith.

DETAILED DESCRIPTION OF THE INVENTION

LEP-10 and LTI are closely related, novel protein protease inhibitors. They are of about the same size as, and share sequence homology with, the SSI family of protease inhibitors.

LEP-10 was originally identified by Coomassie Brilliant Blue staining of SDS-PAGE protein gels as a low molecular weight (about 10,000 daltons) exported protein present in the medium of a culture of *Streptomyces lividans* strain 1326. Amino acid sequence data obtained on peptides derived from a tryptic digest of LEP-10 suggested homology with PSN and SSI. Using the amino acid sequence of one of the LEP-10 tryptic peptides, oligonucleotide probes were prepared and used to identify DNA fragments present in *S. lividans* 1326 chromosomal library which contained a putative LEP-10 sequence. Plasmids containing such putative sequences were used to transform *S. albus*, which does not naturally produce LEP-10 and transformants were shown to express LEP-10.

LTI was similarly originally identified on protein gels from a culture of *S. longisporus*. Preliminary amino acid sequencing thereof indicated homology with LEP-10. Initial screening of a *S. longisporus* library with the LEP-10 oligonucleotide probes resulted in obtainment of chromosomal DNA fragments which hybridized to the LEP-10 probes but which did not code for LTI. A polyclonal antibody was raised against LTI. The anti-LTI antibody reacted with protein produced by the *S. longisporus* but not with LEP-10. Then, by probing with polynucleotide fragments containing the LEP-10 coding sequence, a 2.1 kilobase pair (kb) Bam HI fragment of *S. longisporus* chromosomal DNA was identified as putatively containing the LTI gene. *S. lividans* 1326, which does not produce LTI, was transformed with a plasmid comprising the 2.1 kb sequence and shown to produce LTI by reaction with the anti-LTI antibody. This procedure, which forms a part of this invention, comprises transforming a *Streptomyces* host with DNA fragments from another microorganism or cell known to produce an exported protein. Transformant clones are then incubated on an agar plate in contact with an adsorbent substrate, e.g., a nitrocellulose filter having 0.2 um pore size, to allow exported proteins to adsorb to the substrate. The substrate is then lifted and dried and assayed for reactivity with antisera specific to the exported protein by standard immunossay techniques. Clones of transformants which reacted with the antisera are selected. The DNA fragment introduced into the transformants can then be sub-cloned.

Thus, this invention includes a method of cloning and identifying DNA sequences which code for an exported gene product which comprises:

1) isolating the gene product from a culture of a producing microorganism or cell and raising specific antisera thereto, 2) cloning fragments of DNA from the producing microorganism or cell into a non-producing strain of *Streptomyces*, 3) contacting the *Streptomyces* transformants from step 2 with an adsorbent substrate and incubating the transformants for a time sufficient to allow proteins exported by the transformants to adsorb to the substrate and then 4) assaying the substrate for reactivity with the antisera from step 1.

Similarly, LEP-10 and LTI coding sequences, or sequences for similar proteases, can be identified and isolated from microbial or cell sources by hybridization probing of chromosomal DNA fragments with single-stranded LEP-10 or LTI coding sequence fragments. Such probe fragments are preferably of at least about 30 nucleotides in length. Thus, this invention also includes a method of identifying DNA coding sequences for protease inhibitors which comprises hybridizing fragments of the LEP-10 or LTI coding sequences to chromosomal DNA fragments of a microorganism or cell.

The LEP-10 and LTI protease inhibitors share homology with each other and with SSI and PSN. LEP-10 and LTI are roughly 80% homologous with each other and roughly 70% homologous with SSI and PSN. Following are the amino acid sequences of mature LEP-10 and mature LTI as determined by amino acid sequencing of tryptic digests and/or DNA sequence analyses. Amino acid analyses were carried out in a Beckman 890M amino acid sequenator (Beckman Instruments, Fullerton, Calif.). The sequences of SSI and PSN from published reports are shown where they differ from LEP-10 and LTI.

```
                                                              10
LEP-10              NH2—SER—LEU—TYR—ALA—PRO—SER—ALA—LEU—VAL—LEU—THR—VAL—
LTI                 NH2—ALA—SER—LEU—TYR—ALA—PRO—SER—ALA—LEU—VAL—LEU—THR—VAL—
PSN                 NH2—GLY—                                          —MET—
SSI    ASP—ALA—PRO—SER—ALA—

20
LEP-10    GLY—HIS—GLY—GLU—SER—ALA—ALA—THR—ALA—ALA—PRO—LEU—ARG—ALA—VAL—
LTI       GLY—HIS—GLY—THR—SER—ALA—ALA—ALA—ALA—ALA—PRO—LEU—ARG—ALA—VAL—
PSN                  —ASN—               —THR—VAL—ASN—    —GLU—
SSI            —LYS—    —VAL—       —THR—THR—              —GLU—

30                                  40
LEP-10    THR—LEU—THR—CYS—ALA—PRO—THR—ALA—SER—GLY—THR—HIS—PRO—ALA—ALA—
LTI       THR—LEU—ASN—CYS—ALA—PRO—THR—ALA—SER—GLY—THR—HIS—PRO—ALA—ALA—
PSN                  —ASN—
SSI                                    —GLY—PRO—

50
LEP-10    ALA—ALA—ALA—CYS—ALA—GLU—LEU—ARG—GLY—ALA—HIS—GLY—ASP—PRO—SER—
LTI       ALA—LEU—ALA—CYS—ALA—ASP—LEU—ARG—GLY—VAL—GLY—GLY—ASP—ILE—ASP—
PSN       LEU—GLN—                        —GLY—            —PHE—ASP—
SSI       GLY—SER—            —ASP—   —ALA—ALA—VAL—GLY—    —LEU—ASN—

60                                  70
LEP-10    ALA—LEU—ALA—ALA—GLU—ASP—SER—VAL—MET—CYS—THR—ARG—GLU—TYR—ALA—
LTI       ALA—LEU—LYS—ALA—ARG—ASP—GLY—VAL—ILE—CYS—ASN—LYS—LEU—TYR—ASP—
PSN            —THR—VAL—ARG—GLY—ASP—    —ALA—          —LYS—GLN—PHE—ASP—
SSI            —THR—ARG—GLY—GLU—ASP—              —PRO—MET—VAL—    —ASP—

80
LEP-10    PRO—VAL—VAL—VAL—THR—VAL—ASP—GLY—VAL—TRP—GLN—GLY—ARG—ARG—LEU—
LTI       PRO—VAL—VAL—VAL—THR—VAL—ASP—GLY—VAL—TRP—GLN—GLY—LYS—ARG—VAL—
PSN                                                     —LYS—ARG—VAL—
SSI                                                     —LYS—ARG—VAL—

90                                  100
LEP-10    SER—TYR—GLU—ARG—THR—PHE—ALA—ASN—GLU—CYS—VAL—LYS—ASN—ALA—GLY—
LTI       SER—TYR—GLU—ARG—THR—PHE—GLY—ASN—GLU—CYS—VAL—LYS—ASN—SER—TYR—
PSN                      —THR—                                —SER—TYR—
SSI            —VAL—    —SER—              —GLU—MET—         —HIS—

LEP-10    SER—ALA—SER—VAL—PHE—THR—PHE—COOH
LTI       GLY—THR—SER—LEU—PHE—ALA—PHE—COOH
PSN       GLY—MET—THR—        —PHE—COOH
SSI       GLY—SER—         —ALA—PHE—COOH
```

The above sequence is substantially accurate and, in any event, is not limiting of the invention. It is understood that other LEP-10 or LTI sequences may be obtained due, for example, to variations which do not significantly affect activity, alternative processing or analytical error.

Both LEP-10 and LTI have been shown to inhibit trypsin in a standard trypsin inhibition assay. See, Travis, *Meth. Enzym.*, 80:755–765 (1981). Thus, both LEP-10 and LTI can be used in medical and other applications in which trypsin inhibition, or other protease inhibition is desired. In comparison to aprotinin, LTI is a weak inhibitor of trypsin. This result is not surprising given that protease inhibitors tend to have different protease specificities, even among the SSI family of inhibitors.

Trypsin inhibitory activity was determined in a chromogenic assay using KABI 2288 as substrate (HO-ILE-PRO-ARG-p-nitroanilide.) Scisson of the ARG-p-nitroanilide bond releases p-nitroaniline which absorbs at 410 nm; thus, the extent of cleavage is measured by the increase in absorbance at 410 nm. This assay was used in qualitative manner to determine the inhibitor activity of LTI and LEP-10. Briefly, serial two fold dilutions of either conditioned medium (CM) or ammonium sulfateoconcentrates (AS) of conditioned medium were mixed with 25 ng of trypsin and the substrate was added. After 30 min at room temperature, the assay was stopped by addition of acetic acid. The assay was carried out in microtiter plates, which were then read in an ELISA reader. Similar samples of PSN were included as controls. The LTI samples had a strong brownish-black pigment which gave a high background in the assay; however, the purified protein shows inhibitory activity as well. The data shown are the absorbances measured following cleavage of the chromogenic substrate by trypsin. The growth medium itself shows no activity (data not shown).

| Reciprocal Dilution | Inhibitor | | | | |
|---|---|---|---|---|---|
| | CM LTI | CM PSN | AS LTI | AS PSN | AS LEP-10 |
| No. Inh. | 0.898 | 0.772 | 0.763 | 0.751 | n.d. |
| 1 | 0.170 | 0.010 | 0.081 | 0.018 | 0.070 |
| 2 | 0.195 | 0.046 | 0.087 | 0.021 | 0.091 |
| 4 | 0.187 | 0.046 | 0.078 | 0.023 | 0.130 |
| 8 | 0.182 | 0.053 | 0.081 | 0.024 | 0.165 |
| 16 | 0.187 | 0.058 | 0.092 | 0.036 | 0.219 |
| 32 | 0.209 | 0.273 | 0.176 | 0.076 | 0.293 |

LEP-10 and LTI both showed high activity compared to PSN. However, because the dilutions used were all too low to reach a 50% inhibition level the activities cannot be closely compared accurately. ("n.d," means more detected.)

The proteins can also be used to inhibit endogenous *Streptomyces* or other proteases and thereby to inhibit degradation of desirable proteinacecus products, including heterologous proteins produced by recombinant DNA techniques. For this purpose, one or both of the inhibitors can be added to a *Streptomyces* or other, e.g., *E. coli, Bacillus*, yeast, insect or mammalian, cell culture. Alternatively, *Streptomyces* strains or other hosts can be genetically engineered to produce one or both inhibitors along with a protein of interest, as described further below.

The proteins can also be used to inhibit degradation of proteins in protease-containing solutions and as laboratory reagents such as in an assay for protease inhibition. LTI, for example, has been demonstrated to inhibit conversion of one-chain tPA to two-chain tPA.

The gene expression unit for LEP-10, that is, the DNA sequence containing the LEP-10 coding sequence and regulatory regions required for transcription and translation, was localized on a 4 kb PstI fragment of *S. lividans* 1326 chromosomal DNA and, furthermore, within a 2.97 kb BamHI-PstI fragment thereof. The LTI gene expression unit was found to be present on a 2.1 kb BamHI fragment of *S. longisporus* chromosomal DNA.

The LEP-10 and LTI gene expression unit can be further isolated by additional restriction endonuclease or endonuclease/exonuclease digests and cloning and expression of fragments thereof or by further DNA sequencing. By similar techniques, the coding sequence alone can be isolated and cloned, such as in an expression vector and the regulatory region alone can be isolated and cloned, such as in a promoter probe vector. More specifically, the coding sequence can be fused in-frame to a promoter in a plasmid. Such plasmid is used to transform a *Streptomyces* or other, e.g., *E. coli, B. subtilis*,yeast insect or mammalian host. Such recombinant host is then cultured and the medium or cell extracts are screened for presence of the inhibitor. Screening can be, for example, by gel electrophoresis of proteins, wherein the inhibitor can be detected as a 10 kd protein, by a trypsin inhibition assay, by immunodetection using anti-LTI or anti-LEP-10 antibody, by hybridization with LTI or LEP-10 probes or fragments, and/or by amino acid composition analysis or sequencing of putative LTI or LEP-10 proteins. Exemplary of promoters known to function in *Streptomyces* are the *Streptomyces* beta-galactosidase promoter, the leftward promoter of lambda (PL), the tyrosinase promoter and promoters of genes conferring antibiotic resistance such as erythromycin resistance, neomycin resistance, and thiostrepton resistance.

The regulatory region of LEP-10 or LTI can be inserted into a promoter probe vector, that is, one having a coding sequence for a readily detectable phenotypic marker such that following insertion of a functional promoter upstream of the marker sequence the sequence is expressed. Exemplary of markers useful in *Streptomyces* are: antibiotic resistance markers, e.g., thiostrepton, kanamycin and the *Streptomyces* β-galactosidase.

The LEP-10 and LTI regulatory regions can be used to express LEP-10 or LTI in the native gene expression unit or to express heterologous polypeptides or proteins in a hybrid gene expression unit as transcriptional or translational fusions. For example, the promoter of either LEP-10 or LTI can be fused in frame upstream of a coding sequence for vaccine antigens, e.g., hepatitis B surface antigen and rabies glycoprotein; or for pharmacologically active proteins, e.g., interleukins, plasminogen activators, other protease inhibitors such as alpha-1-antiprotease, tumor necrosis factor, Factor VIII and influenza NS1. The export signal of LEP-10 or LTI can likewise be isolated and ligated to a coding sequence for a polypeptide which is not normally excreted, in frame and downstream of a promoter.

Functional derivatives of each domain within the gene expression units of the invention, i.e., promoter functions, export functions, and protease inhibition functions, can be prepared by use of restriction endonucleases, random mutagenesis such as by ultraviolet irradiation and site directed mutagenesis such as by insertion, addition or substitutions of synthetic oligonucleotides. Such derivatives can readily be checked for effect on function. See, e.g., Davis et al., "Adv. Bact. Genetics", Cold Spring Harbor Laboratory (1980); Miller, "Experiments in Molecular Genetics", Unit III, Cold Spring Harbor Laboratory (1972); Botstein et al., *Science* 229:1193 (1985); and Estell et al., *Science* 233:659

(1986). Functional derivatives of the coding sequences, and of variant proteins produced thereby, are included within the scope of this invention.

Functional derivatives of the proteins can also be prepared by directly altering the proteins. This can be accomplished by chemical means including cleavage to remove amino acids and insertion or addition of amino acids. Such chemically prepared derivatives can be checked for activity such as by a trypsin inhibition assay. Functional chemically prepared derivatives are also included in the scope of the invention.

It appears that LTI is expressed as prepro LTI, having a signal sequence which apparently is cleaved on secretion and a pro sequence which is cleaved extracellularly. In *S. longisporus*, two molecular weight species are secreted. The putative pro LTI has 6 additional amino acids at the N-terminus, compared to mature LTI. In *S. lividans*, two molecular weight species are also observed, but N-terminal amino acid sequence analysis indicates that the processing sites in *S. lividans* may be different than in *S. longisporus*.

Following is the DNA sequence for the LTI coding sequence and for some upstream and downstream untranslated regions. The putative signal and extracellular cleavage sites in *S. longisporus* are indicated in the sequence by slashes (/). The putative signal and extracellular cleavage sites in *S. lividans* are 3 amino acids and 1 amino acid, respectively, downstream (3').

```
 -140       -130       -120       -110       -100            SstII        -80
  *          *          *          *          *               ↓            *
TTCAACACGC AAGGTTACTG AAACACATGG GGTCGAGGTG TTTTTCCGCG GCGGTACATG CGTGCGACTC

-70        -60        -50        -40        -30        -20        -10
  *          *          *          *          *          *          *
GCGCTCGCCG GTCCGGCACC AAACCGGAAC GGGTCGGCAC ACCCTCGAAT CCTGCGGAAG GATGCACACA 10         20         30         40         50
              *          *          *          *          *
ATG CGG AAC ACC GCG CGC TGG GCA GCC ACC CTC GCC CTC ACG GCC ACC GCC GTC TGC
met arg asn thr ala arg trp ala ala thr leu ala leu thr ala thr ala val cys 60          70         80                    100        110
  *           *          *                      *          *
GGA CCC CTC ACC GGA GCC GCG CTC GCC ACC CCG GCC GCT GCT CCC GCC TCG CTC TAC
gly pro leu thr gly ala ala leu ala / Thr Pro Ala Ala Ala / Pro Ala Ser Leu Tyr NotI
    120         130        140        150                ↓          170
     *           *          *          *                             *
GCC CCC TCG GCC CTG GTG CTC ACC GTC GGC CAC GGC ACA AGC GCG GCC GCC GCG GCC
Ala Pro Ser Ala Leu Val Leu Thr Val Gly His Gly Thr Ser Ala Ala Ala Ala Ala 180        190        200        210        220
         *          *          *          *          *
CCG CTG CGG GCC GTC ACC CTG AAC TGC GCC CCG ACG GCC GCC GGA ACC CAT CCG GCC
Pro Leu Arg Ala Val Thr Leu Asn Cys Ala Pro Thr Ala Ser Gly Thr His Pro Ala 230        240        250        260        270        280
 *          *          *          *          *          *
gcn gcn CTC GCC TGC GCC GAC CTG GCG GGG GC GGC GGT GAC ATC GAC GCC CTG AAG
Ala Ala Leu Ala Cys Ala Asp Leu Arg Gly Val Gly Gly Asp Ile Asp Ala Leu Lys 290        300        310        320        330        340
     *          *          *          *          *          *
GCG CGA GAC GGC GTG ATC TGC AAC AAG CTG TAC GAC CCG GTC GTC GTC ACG GTC GAC
Ala Arg Asp Gly Val Ile Cys Asn Lys Leu Tyr Asp Pro Val Val Val Thr Val Asp 350        360        370        380        390
         *          *          *          *          *
GGA GTC TGG CAG GGC AAG CGC GTC TCC TAC GAA CGG ACC TTC GGC AAC GAG TGC GTG
Gly Val Trp Gln Gly Lys Arg Val Ser Tyr Glu Arg Thr Phe Gly Asn Glu Cys Val 400        410        420        430        440        450
 *          *          *          *          *          *
AAG AAC TCC TAC GGG ACC AGC CTC TTC GCG TTC TGA GAGA CCGGGATCGCG GAGTCCTCGT
Lys Asn Ser Tyr Gly Thr Ser Leu Phe Ala Phe —

460        470        480        490        500        510        520
 *          *          *          *          *          *          *
 GCACACCTGA AGAGGCACGC AGTTGGGGAG TGCGAGTCCC TTGTCGCGG TACCCGTCGA TTCGACGCnA
```

It is to be understood that the above sequence is substantially accurate and, in any event, is not limiting of the invention. For example, the illustrated sequence may be incorrect in one or a few base pairs and/or amino acids. Also, other sequences which also code for LTI may exist or may be fabricated, which other sequences may differ in one or a few base pairs and/or amino acids. Such other sequences are expected to be at least about 90% homologous with the illustrated DNA sequence. Also, cleavage of the pre and pro sequences may actually occur at different or additional sites.

The relative amounts of pro LTI and mature LTI can be manipulated. *S. longisporus* cultured in trypticase soy broth buffered with 100 mM MOPS ( 4-morpholinepropane-sulfonic acid) (pH 7.0) buffer (Sigma Chemical Co., St. Louis, Mo.) for 48 to 78 hours yields predominantly pro LTI.

Following is the DNA sequence of the LEP-10 coding sequence and for same upstream and downstream sequences. The signal cleavage site is indicated. As is the case of the sequence for LTI, illustrated above, the following sequence is substantially accurate and is not limiting of the invention.

```
      -390           -380           -370           -360           -350           -340
       *              *              *              *              *              *
GCA CGG GGA TGT AGG GGA GTC GGG CGG AGG CCG CGA CCG AGG CCA GGG CGC GTC CCG

-330           -320           -310           -300           -290           -280
          *              *              *              *              *              *
GCG TGC ACC GAC AGC AGG TTG TCC ATC CGC GCC GCC ACC AGC TCC CGG TCG CGG CCC

-270           -260           -250           -240           -230
               *              *              *              *              *
AGG TAG CCG GGG GCT CCA CGG AGT GCG TCA TCA GGT CCC AGC CGG TGA ACC TCG CCG

-220           -210           -200           -190           -180           -170
 *              *              *              *              *              *
GCC AGC CCC GCC TCG TCC TCC AGG AAC GCT AAT CAA GAA ACG CCC AGT TCC GGA CTT

-160           -150           -140           -130           -120           -110
       *              *              *              *              *              *
GGA ACG TTC TAA TTC TGT GAC TTC ACG CCA CTG ATT CAA TAC GCA AGG TTA CCG AAC

-100            -90            -80            -70            -60
             *              *              *              *              *
ACC GTG GGG TCG AGA TGA GTT TGC GTG CCG GGA CTC GGC AGA CTC GCC GCT CCG GCA

-50            -40            -30            -20            -10             1
 *              *              *              *              *              *
CCG ACC GGG TGC ACC GGC ACC ACC CTC GAA ACG AGC GGA AGG ATG CAC ACA ATG CGG
                                                                Met Arg 10             20             30             40             50             60
        *              *              *              *              *              *
AAC ACC GCG CGC TGG GCA GCG ACT CTG GGC CTG ACG GCC ACC GCC GTC TGC GGG CCC
Asn Thr Ala Arg Trp Ala Ala Thr Leu Gly Leu Thr Ala Thr Ala Val Cys Gly Pro

SIGNAL
       70             80             90            100  CLEAVAGE 110            120
        *              *              *              *         |  *              *
CTC GCC GGG GCC TCC CTC GCC TCC CCG GCC ACC GCC CCC GCG|TCG CTC TAC GCC CCC
Leu Ala Gly Ala Ser Leu Ala Ser Pro Ala Thr Ala Pro Ala|Ser Leu Tyr Ala Pro 130            140            150            160            170
               *              *              *              *              *
TCG GCC CTG GTG CTG ACC GTG GGG CAC GGA GAG AGC GCT GCC ACC GCC GCA CCC CTG
Ser Ala Leu Val Leu Thr Val Gly His Gly Glu Ser Ala Ala Thr Ala Ala Pro Leu 180            190            200            210            220            230
 *              *              *              *              *              *
CGC GCG GTC ACC CTG ACC TGC GCC CCG ACC GCC TCC GGC ACC CAC CCG GCG GCC GCC
Arg Ala Val Thr Leu Thr Cys Ala Pro Thr Ala Ser Gly Thr His Pro Ala Ala Ala 240            250            260            270            280            290
        *              *              *              *              *              *
GCG GCC TGT GCC GAA CTG CGC GCC GCG CAC GGC GAC CCG AGT GCC CTG GCC GCC GAG
Ala Ala Cys Ala Glu Leu Arg Ala Ala His Gly Asp Pro Ser Ala Leu Ala Ala Glu 300            310            320            330            340
               *              *              *              *              *
GAC TCG GTG ATG TGC ACC CGG GAG TAC GCC CCC GTG GTC GTC ACC GTC GAC GGC GTC
Asp Ser Val Met Cys Thr Arg Glu Tyr Ala Pro Val Val Val Thr Val Asp Gly Val 350            360            370            380            390            400
 *              *              *              *              *              *
TGG CAG GGG CGG CGC CTC TCC TAC GAA CGC ACC TTC GCC AAC GAG TGC GTG AAG AAC
Trp Gln Gly Arg Arg Leu Ser Tyr Glu Arg Thr Phe Ala Asn Glu Cys Val Lys Asn 410            420            430            440            450            460
        *              *              *              *              *              *
GCG GGC AGC GCG AGC GTC TTC ACG TTC TGA GGG ACC GGG ACC GCC GGA CTG CGC GTG
Ala Gly Ser Ala Ser Val Phe Thr Phe ———

470            480            490            500            510
               *              *              *              *              *
ATC GGC TGC TCG CTA CTG GGG AGT GCG AGC GCC GCC GTA CGG GTC CCG CGG GCC CGC
```

```
520         530         540         550         560         570
 *           *           *           *           *           *
ACC GGG GAC GGC GGA CGG AGT GGG GCC GTC CGC CGT TCT CCC GGT TCA GGG GCA CGG 580         590         600         610         620         630
 *           *           *           *           *           *
TCG GCC GTT CGC GGC CGG GCC GTC CGC GGC CCT GGC GGA CCG GGC ACG GTG GCT GTG 640         650
 *           *
TCG CAC CAC GGA TAG CGC CGA CTG
```

The LEP-10 and LTI proteins, as noted above, were originally discovered as products of *S. lividans* 1326 and *S. longisporus*. It is likely, however, that other strains and species produce the same or substantially the same proteins, i.e., substantially homologous (>90%, especially >95%) and substantially the same substrate (protease) specificity and activity. Also, the LEP-10 and LTI proteins can be synthesized by standard protein synthesis techniques or DNA coding sequences therefor can be synthesized by standard DNA synthesis techniques. Thus, the invention includes the LEP-10 and LTI proteins and gene expression units and functional domains thereof regardless of source.

Oligonucleotide probes for detecting similar DNA sequences in other strains and species can be synthesized based on the LEP-10 and LTI sequences. However, as noted above, results of probing with such oligonucleotides may produce false positives. Therefore, probing initially or secondarily with larger DNA fragments, e.g., greater than about 30 nucleotides, and preferably greater than about 50 nucleotides, is preferred. By such probing techniques, genes encoding the same inhibitors or other inhibitors of the SSI family can be identified.

By recombinant DNA techniques, the coding sequences of the invention can be used to produce large quantities of LEP-10 and LTI. These techniques comprise, in sum, transformation of a host, bacterial or eukaryotic, with a gene expression unit comprising the LEP-10 or LTI coding sequence of the invention. For this purpose, the native gene expression unit on a plasmid or other vector or a hybrid gene expression unit comprising the inhibitor coding sequence and a heterologous regulatory region can be used. The inhibitors so produced are purified to a desirable extent by standard protein isolation techniques.

The following Examples are illustrative, and not limiting of the invention.

EXAMPLES

Example 1. LEP-10

*S. lividans* strain 1326 (Agricultural Research Culture Collection, Peoria, Ill., NRRL 15091) was cultured in SL-glycerol, SL-glucose and YEMES broths at 28° C. for approximately 30 hours. After spinning down the cells by low speed centrifugation, the supernatants were concentrated by ammonium sulfate precipitation, redissolved and electrophoresed on SDS-PAGE (15%) gels to separate protein products. Upon staining with Coomassie Brilliant Blue R-250, a dense band corresponding to a protein having a molecular weight of about 10,000 daltons was identified as having been expressed in certain broths. SL medium comprises components SL-A and SL-B and a trace elements solution as follows:

| SL-A | |
|---|---|
| (NH₄)₂SO₄ | 1.0 g/l |
| L-asparagine | 2.0 g/l |
| K₂HPO₄ | 9.0 g/l |
| NaH₂PO₄ | 1.0 g/l |
| SL-B | |
| yeast extract | 20 g/l |
| MgCl₂.6H₂O | 5.0 g/l |
| CaCl₂.H₂O | 0.1 g/l |
| trace elements sol. | 20 ml/l |
| Trace elements sol. | |
| ZnCl₂ | 40 mg/l |
| FeCl₂.2H₂O | 200 mg/l |
| CuCl₂.2H₂O | 10 mg/l |
| MnCl₂.4H₂O | 10 mg/l |
| Na₂B₄O₇.10H₂O | 10 mg/l |
| (NH₄)₆Mo₇O₂₄.4H₂O | 10 mg/l |

SL-A is autoclaved and SL-B is filter sterilized prior to adding together in a ratio of 1:10 SL-B: SL-A (v/v). To prepare SL-glucose and SL-glycerol, 1% (w/v) glucose and glycerol, respectively, are added.

Samples of the protein were cut out and removed from gels. The protein was reduced and S-dansylamidoethylated with dansylazridine. The alkylated protein was digested with trypsin and the tryptic peptides were recovered by reverse phase HPLC. Individual peptides were sequenced in a Beckman sequenator to-obtain the primary structure data reported above.

Based on the amino acid sequence, a series of single stranded oligonucleotide probes were prepared. Probe #263 was a mixed 24-mer as follows:

These probes were used to probe a Charon phage library of *S. lividans* 1326 chromosomal DNA prepared substantially as described by Maniatis et al., "Molecular Cloning-A Laboratory Manual," 1982, Cold Spring Harbor Laboratory.

The recombinant phage, Charon 25.5 (Ch25.5), contains *Streptomyces lividans* 1326 chromosomal DNA which hybridizes to the mixed otigonucleotide probe #263. This probe is complementary to the LEP-10 mRNA. A BglII-EcoRI fragment (about 18 kb) of Ch 25.5 was cloned into the Bam HI-EcoRI site of plasmid pUC18 to yield plasmid pD1.

From pD1 was isolated a PstI fragment (about 4 kb) which also hybridized with the oligonucleotide probe. This PstI fragment was cloned into the PstI site of pBR322 to yield plasmid pBR33. The 4 kb PstI fragment contains a BamHI-PstI fragment (about 2.97 kb) fragment which hybridizes with oligonucleotide probe.

Both the 4 kb PstI and the 2.97 kb Bam HI-PstI fragments were cloned into the shuttle plasmid vector pMB157, which is a low copy number *E. coli-Streptomyces* shuttle vector comprising SCP2 stability and replication functions, pUC8 sequences and thiostrepton and ampicillin resistance. The recombinant plasmids pMB157-21 and pMB157-8 (which contain the 2.97 kb BamHI-PstI fragment) and pMB157-22 (which contains the 4 kb PstI fragment) were transformed into protoplasts of *S. albus* which was previously shown not to produce LEP-10. Colonies of transformants were checked for the production of LEP-10 protein by immunoblotting. Nitrocellulose filters (0.2 um) were applied directly to plates containing colonies of the transformants. After the filters were removed from the plates they were processed with antibody to LEP-10 by the Western blot procedure. Transformants of *S. albus* containing the recombinant plasmids produced extracellular LEP-10 as determined by this immunoblot procedure. LEP-10 in culture supernatants of *S. albus* (pMB157-22) and *S. albus* (pMB157-21) grown in SL-glycerol medium was also detected by Western blots of SDS-PAGE gels. Thus, all of the information necessary to produce a mature extracellular LEP-10 protein in *S. albus* is present on the 2.97 kb Bam HI-PstI fragment.

Partial sequence of the LEP-10 gene has been identified on an RsaI fragment (about 180 bp) isolated from the recombinant phage Ch25.5. This RsaI fragment is present in both the aforementioned 4 kb PstI and the 2.97 kb BamHI-PstI fragments. The RsaI fragment contains a sequence encoding the carboxy-terminal one-third of the LEP-10 protein.

Example 2. LTI

Using the oligo LEP-10 probes described in Example 1 above, regions of homology were identified in chromosomal DNA of *S. longisporus* (ATCC 23931) previously shown to produce a small exported protein of about 10 kd having N-terminal amino acid sequence homology with LEP-10. DNA sequence data subsequently showed that such DNA fragments did not code for a LEP-10-like protein.

An alternative approach, involving cloning the LTI gene in *Streptomyces* and identifying the clones by screening with anti-LTI antibody, was employed. Antibody against purified LTI was raised in rabbits and found to react with LTI but not with LEP-10. This antibody was also found to react with protein produced by colonies of *S. longisporus* adsorbed to 0.2 um nitrocellulose filters following 4 hours incubation at 28° C. but not with protein produced by *S. lividans*. Detection was enhanced by detection of the LTI-antibody complex using biotinylated goat anti-rabbit IgG and streptavidin-biotin-biotinylated horseradish peroxidase complex (a Vectastain kit, Vectastain Laboratories, Burlingame, Calif.). For cloning, a 2.1 kb BamHI fragment was identified in *S. longisporus* DNA using three different LEP-10 fragment probes including the RsaI fragment. 2–2.3 kb sized BamHI fragments were cloned into plasmid pIJ703 (Katz et al., *J. Gen. Microbiol.* 129:2703–2714 (1983)) (BglII-cut) and transformed into *S. lividans*. Transformants were screened with anti-LTI antibody to identify a positive clone. (A higher frequency was obtained through use of a low copy number vector in a comparable experiment.)

This positive clone was in a group of six colonies and had to be picked and rescreened. Plasmid DNA from positive colonies was isolated and shown to contain an insert of about 2.1 kb. Culture supernatants (trypticase soy broth, 28° C., 48 hrs) from these positives were spotted on nitrocellulose filters as described above and probed with anti-LTI antibody and found to be positive. Transformation of *S. lividans* and of *S. albus*, both of which were previously shown not to produce LTI, with plasmid DNA resulted in production of LTI as shown by western analysis and trypsin inhibition of *S. albus* supernatants. Southern blots were probed with a DNA fragments containing the RsaI fragment from LEP-10 and hybridization was observed to the insert.

LTI is harvested from *Streptomyces longisporus* conditioned medium by ammonium sulfate precipitation (65% saturation). The precipitate, which floats, is collected by centrifugation which causes the "precipitate" to form a dense mat floating on the surface of the liquid. This mat is recovered and resuspended in 10 mM ammonium acetate pH 6.0, and dialyzed against 50 to 100 volumes of the same buffer for 16 to 18 hours. The dialyzed sample is harvested and the large amount of dark brown fibrous material remaining insoluble is removed by centrifugation. The clarified supernatant is applied to a carboxymethyl cellulose column (CM-52, Whatman) equilibrated in the dialysis buffer. After unbound protein is washed through, the column is developed with a linear gradient from 10 to 250 mM ammonium acetate, pH 6.0. The LTI elutes at approximately 150 mM ammonium acetate. The pooled LTI peak is dialyzed against 10 mM ammonium acetate, pH 6, and stored at 4° C.

Example 3. Heterologous Gene Expression and secretion using LTI regulatory regions pLTI520 is pUC 18 (Yanisch-Perring et al., *Gene* 33:103 (1985)) containing the entire LTI coding sequence and about 410 upstream base pairs on a 920 base pair. SacI-KpnI fragment of *S. longisporus* chromosomal DNA. A. filled-in BanI fragment of the interleukin-1 beta (1L-1B) (Myers et al., *J. Biol. Chem.* (in press)), which lacks a regulatory region, was ligated to the LTI sequence at the NotI site (between bases 158 and 159 in the above-illustrated DNA sequence for LTI); the NotI site was blunt-ended by treatment with mung bean nuclease prior to ligation.

A XmnI-BamHI fragment of pLTI520, containing the LTI - IL-1B fusion, was inserted into pSK02 (Brawner et al., *Gene* 40:191 (1986)). The XmnI site is in the ampicillin resistance gene in pUC 18. The BamHI site is in the polylinker region upstream of lac Z in pUC 18.

The pSK02 derivative was transformed in a galK deficient mutant strain of *S. lividans* 1326, strain 12K (Brawner et al., cited above). After sporulation, transformants were inoculated into trypticase soy broth (TSB) and incubated at 28° C. for at least 72 hours.

Both supernatants and cell extracts were analyzed by SDS-PAGE and western immunoblotting. These analyses showed expression and secretion of two proteins, both of which reacted with polyclonal anti-IL-1B. One of the two appeared to be mature IL-1B. The other had a slower mobility consistent with that expected for IL-1B fused to 17 amino acids of mature IL-1B.

Example 4. Heterologous gene expression and secretion using LEP-10 regulatory regions A LEP-10-IL-1B fusion was constructed in pUC 18. The fusion contained *S. lividans* DNA from a HinfI site (between bases −132 and −133 in the above-illustrated sequence for LEP-10) to a cut-back BglI site (between bases 85 and 86). The blunt-ended BglI site was ligated to a filled-in AvaI site in pUC18. Then, a DNA fragment containing the BanI IL-1B fragment with a BamHI linker was ligated to a BamHI site in pUC 18 to yield the construction illustrated as follows:

| 1 | 2 | 3 | 4 |
|---|---|---|---|
| \|*CTC GCC T|CC GGG| GAT CCG| GCA CCT*\| | | | | wherein region 1 is derived from LEP-10, region 2 is derived from pUC 18, region 3 is from the linker and region 4 is the 1L-1B coding sequence. Maintenance sequences from the *Streptomyces* vector, pIJ102 (Kieser et al., *Mol. Gen. Genet.* 185:223 (1982)), were then inserted.

Following transformation of *S. lividans* 12K and culturing transformants in trypticase soy broth, an extracellular protein which corresponds approximately to mature IL-1B was observed by western immunoblotting. Although N-terminal sequence analysis of the excreted protein has not been carried out, it appears that cleavage may occur between the first residue (alanine) and the second residue (proline) of IL-1B to remove the LEP-10 signal sequence.

Examples 4 and 5 demonstrate utility of the LEP-10 and LTI regulatory regions both to express heterologous gene products in *Streptomyces* and to export heterologous gene products which are not otherwise exported.

The above description and examples fully describe the invention and preferred embodiments thereof. The invention, however, is not limited to precisely the embodiments described but also include all modifications coming within the scope of the claims which follow.

We claim:

1. A process for producing a heterologous polypeptide in Streptomyces which comprises transforming a Streptomyces organism with a recombinant DNA molecule comprising an LEP-10 or LTI sequence selected from the group consisting of a sequence encoding a gene expression unit, a promoter sequence or an export control encoding sequence operatively linked to a heterologous coding sequence and then culturing the transformed Streptomyces such that the heterologous polypeptide is expressed.

\* \* \* \* \*